United States Patent

Shiobara et al.

[11] Patent Number: 5,336,786
[45] Date of Patent: Aug. 9, 1994

[54] ORGANIC SILICON COMPOUNDS

[75] Inventors: Toshio Shiobara; Koji Futatsumori; Satoshi Okuse; Takayuki Aoki; Miyuki Wakao; Shigeki Ino, all of Annaka, Japan

[73] Assignee: Shin-Etsu Chemical Company, Limited, Tokyo, Japan

[21] Appl. No.: 160,912

[22] Filed: Dec. 3, 1993

[30] Foreign Application Priority Data

Dec. 7, 1992 [JP] Japan ................... 4-351267

[51] Int. Cl.$^5$ .................. C07F 7/08; C07D 303/02
[52] U.S. Cl. ................................. 549/215
[58] Field of Search ........................ 549/215

[56] References Cited

U.S. PATENT DOCUMENTS

| | | | |
|---|---|---|---|
| 3,660,434 | 5/1972 | Patterson | 549/215 X |
| 4,861,901 | 8/1989 | Lau et al. | 549/215 X |
| 4,954,580 | 9/1990 | Zahir | 549/215 X |
| 5,258,139 | 11/1993 | Ichimura et al. | 549/215 X |
| 5,260,455 | 11/1993 | Eckberg | 549/215 |

Primary Examiner—Paul F. Shaver
Attorney, Agent, or Firm—Birch, Stewart, Kolasch & Birch

[57] ABSTRACT

Novel organic silicon compounds are based on a benzene ring having two epoxy radicals and an alkoxysilane radical. They are useful as resin modifiers, adhesive aids for epoxy resins, and silane coupling agents. Inorganic fillers such as silica surface treated with the compounds are useful in encapsulating resin compositions.

6 Claims, No Drawings

ORGANIC SILICON COMPOUNDS

BACKGROUND OF THE INVENTION

1. Field of the Invention

This invention relates to organic silicon compounds of the structure including a benzene ring having attached thereto two epoxy radicals and an alkoxysilane through a propylene linkage which are useful as resin modifiers, adhesive aids for epoxy resins, and silane coupling agents.

2. Prior Art

Semiconductor elements such as transistors, ICs and LSIs are generally enclosed in ceramic and plastic packages before they are ready for use as semiconductor devices. Among these packages, the ceramic packages are resistant against heat and humidity since they are made of materials which themselves are heat resistant and impermeable. In addition, the ceramic packages have high mechanical strength because of hollow packages, providing a highly reliable seal. The ceramic packages, however, have the drawbacks including relatively costly materials and low yields on mass scale production. Instead, resin encapsulation using plastic packages becomes the current mainstream of packaging technology. This type of resin encapsulation heretofore uses epoxy resin compositions with successful results.

Technical innovations developed in the semiconductor field have brought further advances in the degree of integration, element size, and refinement of wiring, which require the packages to be reduced in size and thickness. It is thus desired that the encapsulating material be further improved in reliability, namely have low stress, reliability under humid conditions, reliability against impact, and crack resistance.

To meet such requirements, several attempts have been made by modifying encapsulation resin with rubber for reducing thermal stresses and by increasing the loading of inorganic fillers, but the results are still unsatisfactory. In order to accommodate an increase in element size, it is strongly desired to improve the encapsulating material with respect to low stress, reliability under humid conditions, reliability against impact, and crack resistance.

SUMMARY OF THE INVENTION

We have found that a novel organic silicon compound of formula (1) can be prepared by adding allyl to a dihydroxybenzene of formula (2) to form a compound of formula (3), epoxidizing the phenolic hydroxyl radicals of the compound of formula (3) to form a compound of formula (4), and effecting hydrosilylation reaction between the compound of formula (4) and a hydroalkoxysilane of formula (5) as shown in the following reaction scheme, all the formulae being shown below.

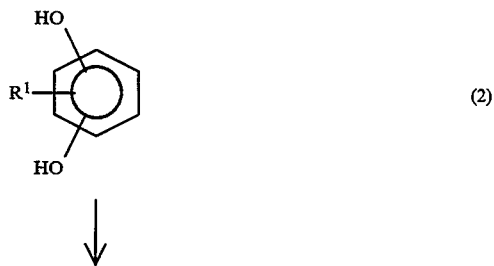

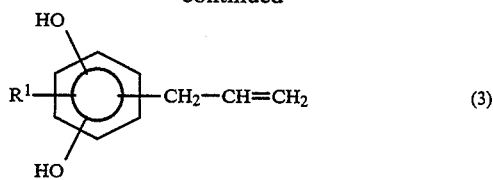

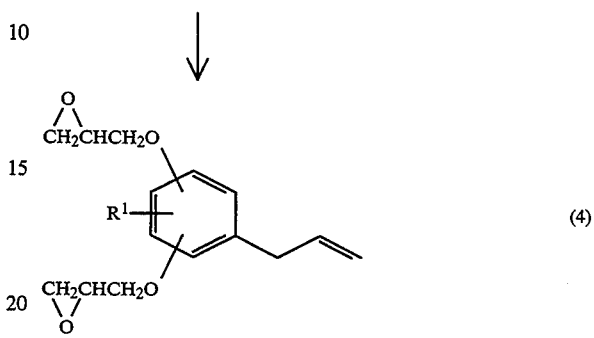

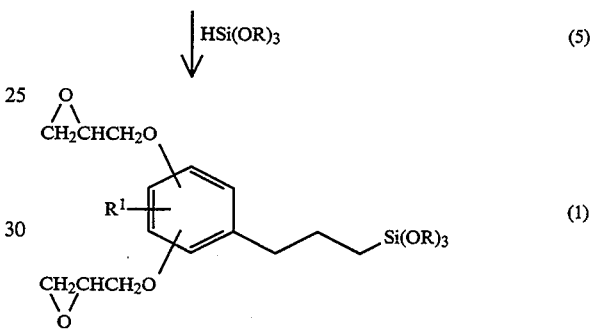

In the formulae, $R^1$ is a hydrogen atom, a substituted or unsubstituted monovalent hydrocarbon radical having 1 to 6 carbon atoms, or a halogen atom, and R is a substituted or unsubstituted monovalent hydrocarbon radical having 1 to 6 carbon atoms.

Since the organic silicon compounds of formula (1) contain epoxy radicals and an alkoxysilane radical as functional radicals in their molecule, they are highly reactive with Si—OH radicals of silica and epoxy or phenolic hydroxyl radicals of various organic compounds. Then the inventive compounds are effective as modifiers for components used in composite materials, typically semiconductor device encapsulating resin compositions, for example, as silica modifiers, resin modifiers or epoxy resin adhesive aids. In such applications, the inventive compounds are effective for increasing the reliability of semiconductor resin encapsulation. The inventive organic silicon compounds are especially useful for the surface treatment of inorganic fillers. If conventional well-known semiconductor encapsulating resin compositions are loaded with inorganic fillers which have been surface treated with the inventive compounds, the compositions will cure into products featuring low stress, reliability under humid conditions, reliability against impact, and crack resistance. Then in another aspect, the inorganic fillers surface treated with the inventive compounds are very advantageous fillers in semiconductor encapsulating resin compositions and improve the reliability of semiconductor device resin encapsulation.

DETAILED DESCRIPTION OF THE INVENTION

The organic silicon compounds of the present invention are of the following general formula (1).

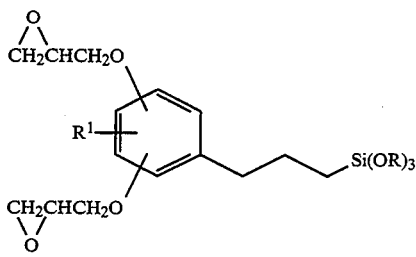
(1)

In the formula, R¹ is a hydrogen atom, a substituted or unsubstituted monovalent hydrocarbon radical having 1 to 6 carbon atoms, or a halogen atom, and R is a substituted or unsubstituted monovalent hydrocarbon radical having 1 to 6 carbon atoms. Examples of the hydrocarbon radical represented by R¹ or R include methyl, ethyl, propyl, t-butyl, propenyl and phenyl radicals.

The organic silicon compounds of formula (1) can be prepared by adding allyl to a dihydroxybenzene of formula (2) followed by epoxidation and hydrosilylation as shown below.

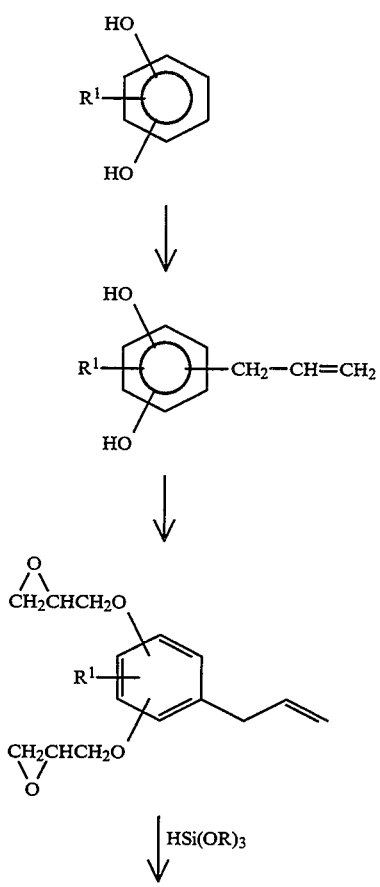

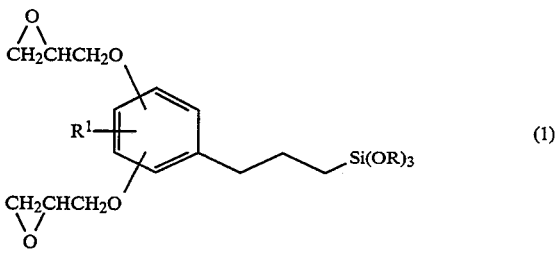
(1)

The starting reactant, dihydroxybenzene of formula (2) may be one corresponding to a particular end organic silicon compound, for example, hydroquinone.

Allyl addition to the dihydroxybenzene (2) can be achieved, for example, by converting the dihydroxybenzene (2) into an allyl ether by a conventional technique, followed by Claisen rearrangement.

Subsequent epoxidation can be done by conventional techniques, for example, by effecting reaction in the presence of dehydrochlorination agents such as sodium hydroxide.

Subsequent hydrosilylation or addition of a hydrogen atom of a silane compound to the allyl group can be done by conventional techniques using platinum series catalysts.

One specific reaction scheme is shown below wherein hydroquinone is used as a typical starting reactant.

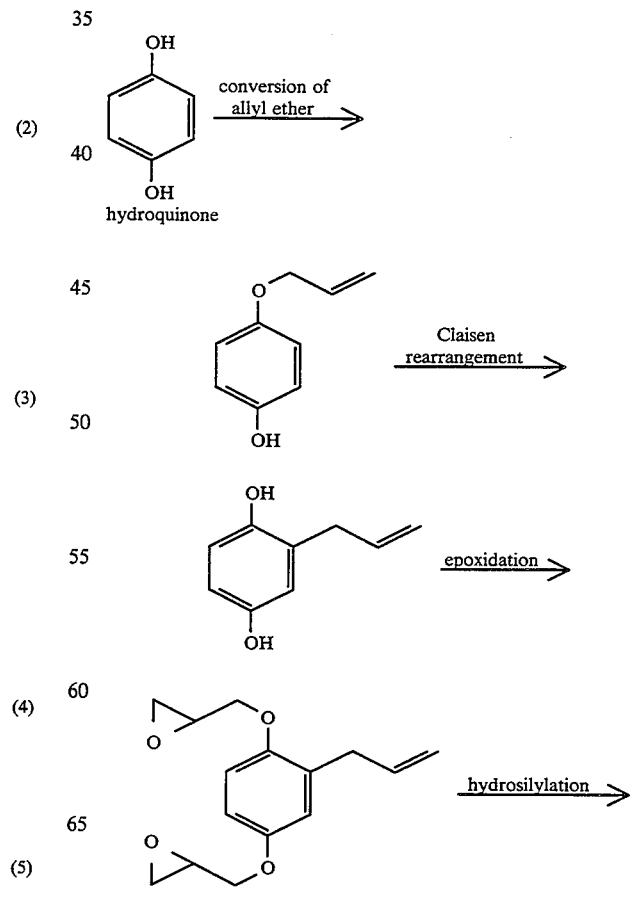

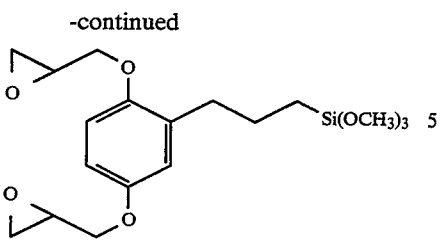

Since the organic silicon compound of the invention contains two epoxy radicals and an alkoxysilane radical as functional radicals in its molecule as is evident from formula (1), it is highly reactive with silanol radicals of silica and epoxy or phenolic hydroxyl radicals of various organic compounds. Then the inventive compound is an effective modifier for inorganic fillers, an effective resin modifier, and an effective adhesive aid for epoxy resins or the like. In the first application, the compound is generally designated a silane coupling agent.

Particularly when inorganic fillers are surface treated with the organic silicon compounds of formula (1), the treated inorganic fillers become useful as fillers for conventional well-known semiconductor encapsulating resin compositions in imparting low stress, reliability under humid conditions, reliability against impact, and crack resistance to cured products thereof.

The type of inorganic filler which can be treated with the inventive compounds is not particularly limited. Included are conventional inorganic fillers, for example, silica fillers, alumina fillers, titanium oxide, iron oxide, and magnesium oxide. The inventive compounds are particularly effective for treating silica fillers. The silica fillers include fused silica, crystalline silica, silicon nitride, colloidal silica, silica aerogel, mica and talc and may be of any desired shape.

Inorganic fillers may be surface treated with the inventive organic silicon compounds by any desired technique. Preferably surface treatment is done such that about 0.01 to 10% by weight, especially about 0.1 to 2% by weight of the inventive organic silicon compound may deposit on the inorganic filler.

One exemplary surface treatment is described wherein silica is an exemplary filler. First by mixing and agitating the organic silicon compound and silica, the silica is coated on the surface. This coating is preferably assisted by diluting the compound with a solvent such as water, alcohol and toluene. The temperature in the coating step is not limited though it is generally about 25° to 120° C. The coating treatment can be promoted by hydrolyzable catalysts such as diazabicycloundecene.

After the coating treatment, the coated silica may be aged at an appropriate temperature for a long time or dried at a high temperature in order to reinforce the bond between the organic silicon compound and the silanol group on the silica surface. More specifically, the coated silica is preferably aged at about 20° to 50° C. for about 1 to 10 hours or dried at about 50° to 200° C. for about 1 to 15 hours.

The inorganic filler thus coated with the organic silicon compound according to the present invention can be blended with conventional epoxy and other resins in conventional amounts to form resin compositions. The resin composition which is to be loaded with the coated inorganic filler may include conventional known components.

EXAMPLE

Examples of the present invention are given below by way of illustration and not by way of limitation.

EXAMPLE 1

Conversion of hydroquinone into allyl ether

A 2-liter four necked flask equipped with a condenser, thermometer and stirrer was charged with 300 grams of hydroquinone in acetone and 330 grams of allyl bromide. With stirring, 377 grams of potassium carbonate was added to the flask where it was dissolved before reaction was effected for 8 hours under reflux. At the end of 8-hour reaction, the reaction mixture was passed through a filter and removed of the solvent. The reaction product was dissolved in 0.8 liters of methyl isobutyl ketone again. Upon washing and distilling off the solvent, there was obtained 105 grams (yield 26%) of a compound A. NMR and IR analysis identified the compound to have the following structural formula.

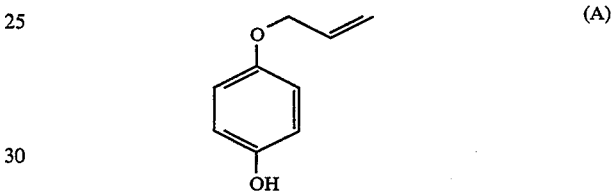

Claisen rearrangement of allyl radical

In a 1-liter four necked flask equipped with a condenser, thermometer and stirrer, 105 grams of Compound A was heated at 180° C. in a nitrogen atmosphere for 30 minutes for reaction. There was obtained 103 grams (yield 98%) of a compound B. NMR and IR analysis identified the compound to have the following structural formula.

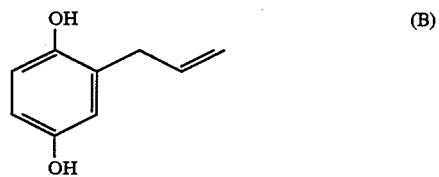

Epoxidation

A 2-liter four necked flask equipped with a condenser, thermometer and stirrer was charged with 90 grams of Compound B, 666 grams of epichlorohydrin, and 4.3 grams of cetyltrimethyl ammonium, which were agitated for 3 hours under reflux. Thereafter, 70 grams of NaOH (50% aqueous solution) was added dropwise to the flask under a vacuum (80° to 90° C./100 to 130 mmHg). At the end of addition, the mixture was passed through a filter, removed of the solvent, washed with 10% NaOH aqueous solution to remove hydrolyzable chlorine, and washed with water, obtaining 75 grams (yield 48%) of a Compound C. NMR and IR analysis identified the compound to have the following structural formula.

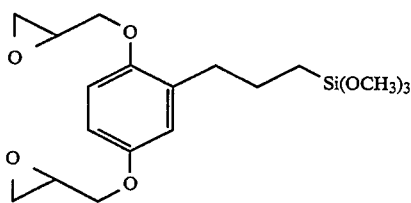

Silylation

A 1-liter four necked flask equipped with a condenser, thermometer and stirrer was charged with 63 grams of Compound C and 450 grams of toluene. After azeotroping off water, 1.8 grams of a platinum chloride series catalyst (PL-50T commercially available from Shin-Etsu Chemical Co., Ltd.) was added to the flask. With stirring, 31 grams of hydrogenated trimethoxysilane was added dropwise to the flask. Thereafter, reaction was effected at 60° C. for three hours. At the end of reaction, the unreacted Compound C and solvent were removed under vacuum, obtaining 24 grams (yield 79%) of an end organic silicon compound of formula (D) shown below. Compound D had the spectral date shown below.

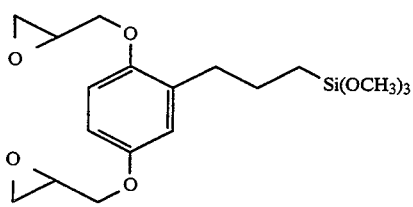

(D)

NMR spectrum, solvent $(CD_3)_2CO$, ppm ($\delta$)

0.6~1.1: —C$\underline{H}_2$—Si(OCH$_3$)$_3$ 1.5~2.1: [C$_6$H$_3$]—CH$_2$—C$\underline{H}_2$—

2.5~3.0: —C$\underline{H}$——CH$_2$ (epoxide)

3.2~3.5: —C$\underline{H}$——CH$_2$ (epoxide)

3.6: —Si(OC$\underline{H}_3$)$_3$ 3.9: —C$\underline{H}_2$—CH——CH$_2$ (epoxide)

4.3: —C$\underline{H}_2$—CH——CH$_2$ (epoxide)

6.5~7.1: [C$_6$H$_3$]

IR spectrum, cm$^{-1}$
 C—H: 2950
 Si—CH$_2$: 1210
 Si—O: 1080
 C—O—C: 1040

(C)

| Elemental analysis (wt %) | | | | |
|---|---|---|---|---|
| | Si | C | O | H |
| Found | 7.34 | 56.01 | 29.60 | 7.05 |
| Calcd. | 7.31 | 56.22 | 29.12 | 7.34 |

EXAMPLE 2

Following the same synthesis route as organic silicon compound D, another organic silicon compound of formula (E) shown below was synthesized. It had the spectral data shown below.

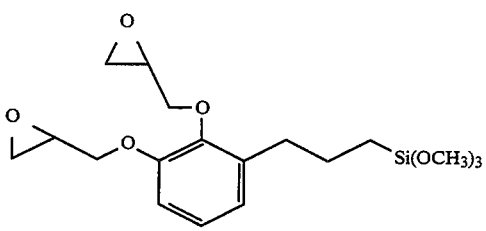

(E)

NMR spectrum, solvent $(CD_3)_2CO$, ppm ($\delta$)

0.5~1.1: —C$\underline{H}_2$—Si(OCH$_3$)$_3$ 1.4~2.0: [C$_6$H$_3$]—CH$_2$—C$\underline{H}_2$—

2.5~3.1: —C$\underline{H}$——CH$_2$ (epoxide)

3.1~3.5: —C$\underline{H}$——CH$_2$ (epoxide)

3.6: —Si(OC$\underline{H}_3$)$_3$ 3.8: —C$\underline{H}_2$—CH——CH$_2$ (epoxide)

4.4: —C$\underline{H}_2$—CH——CH$_2$ (epoxide)

6.6~7.2: [C$_6$H$_3$]

IR spectrum, cm$^{-1}$
 C—H: 2960
 Si—CH$_2$: 1220
 Si—O: 1070
 C—O—C: 1030

| Elemental analysis (wt %) | | | | |
|---|---|---|---|---|
| | Si | C | O | H |
| Found | 7.38 | 56.15 | 29.22 | 7.25 |
| Calcd. | 7.31 | 56.22 | 29.12 | 7.34 |

EXAMPLE 3

Following the same synthesis route as organic silicon compound D, another organic silicon compound of formula (F) shown below was synthesized. It had the spectral data shown below.

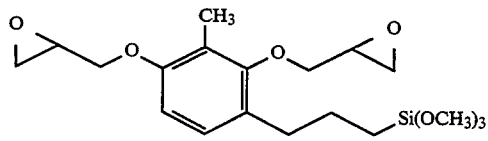 (F)

NMR spectrum, solvent (CD3)2CO, ppm (δ)

0.6~1.0: —C$\underline{H_2}$—Si(OCH3)3

1.6~2.1: [C6H2]—CH2—C$\underline{H_2}$—

2.3:[C6H2]—CH3

2.6~3.1: 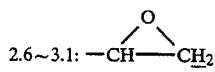

3.2~3.6: 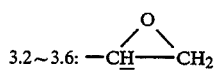

3.6: —Si(OC$\underline{H_3}$)3

3.8: —C$\underline{H_2}$—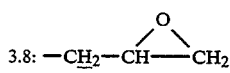

4.2: —CH2—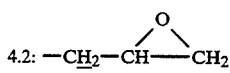

6.6~7.3: [C6H2]

IR spectrum, cm$^{-1}$
C—H: 2950
Si—CH2: 1200
Si—O: 1080
C—O—C: 1010

| Elemental analysis (wt %) | | | | |
|---|---|---|---|---|
| | Si | C | O | H |
| Found | 7.10 | 57.30 | 28.01 | 7.59 |
| Calcd. | 7.05 | 57.26 | 28.10 | 7.59 |

EXAMPLE 4

A 3-liter four necked flask equipped with a reflux condenser, stirrer and addition funnel was charged with 1 kg of spherical fused silica (mean particle size 25 μm), 11.4 grams of organic silicon compound D synthesized in Example 1, 100 grams of water, and 1 kg of isopropyl alcohol as a solvent, which were agitated at 82° C. for 2 hours. The solvent was distilled off from the reaction mixture under vacuum. Subsequent drying at 120° C. for 15 hours yielded 1 kg of treated silica.

EXAMPLE 5

A 3-liter four necked flask equipped with a reflux condenser, stirrer and addition funnel was charged with 1 kg of spherical fused silica (mean particle size 25 μm), 11.4 grams of organic silicon compound E synthesized in Example 2, 100 grams of water, and 1 kg of isopropyl alcohol as a solvent, which were agitated at 82° C. for 2 hours. The solvent was distilled off from the reaction mixture under vacuum. Subsequent drying at 120° C. for 15 hours yielded 1 kg of treated silica.

EXAMPLE 6

A 3-liter four necked flask equipped with a reflux condenser, stirrer and addition funnel was charged with 1 kg of spherical fused silica (mean particle size 25 μm), 11.8 grams of organic silicon compound F synthesized in Example 3, 100 grams of water, and 1 kg of isopropyl alcohol as a solvent, which were agitated at 82° C. for 2 hours. The solvent was distilled off from the reaction mixture under vacuum. Subsequent drying at 120° C. for 15 hours yielded 1 kg of treated silica.

COMPARATIVE EXAMPLE 1

Spherical fused silica (mean particle size 25 μm) was used without treating with the organic silicon compound.

COMPARATIVE EXAMPLE 2

A 3-liter four necked flask equipped with a reflux condenser, stirrer and addition funnel was charged with 1 kg of spherical fused silica (mean particle size 25 μm ), 7.11 grams of γ-glycidoxypropyltrimethoxysilane (KBM-403 commercially available from Shin-Etsu Chemical Co., Ltd. ), 100 grams of water, and 1 kg of isopropyl alcohol as a solvent, which were agitated at 82° C. for 2 hours. The solvent was distilled off from the reaction mixture under vacuum. Subsequent drying at 120° C. for 15 hours yielded 1 kg of surface treated silica.

Tests

Using a hot two-roll mill, encapsulating epoxy resin compositions were prepared by melting and milling the resin and other components shown in Table 1 together with the treated silica samples of Examples 4 to 6 and Comparative Example 2 and the untreated silica of Comparative Example 1.

The compositions are examined by the following tests. The results are also shown in Table 1.

Water absorptivity

The composition was molded at 180° C. and 70 kg/cm$^2$ for a molding time of 2 minutes into a disk having a diameter of 70 mm and a thickness of 2 mm and post-cured at 180° C. for 4 hours. The disk was allowed to stand in a 120° C./RH 100% atmosphere for 24 hours before water absorptivity was determined.

Dielectric dissipation factor

The composition was molded at 180° C. and 70 kg/cm$^2$ for a molding time of 2 minutes into a disk having a diameter of 70 mm and a thickness of 2 mm and post-cured at 180° C. for 4 hours. The disk was allowed to stand in a pressure cooker at 120° C. for 120 hours before dielectric dissipation factor was determined.

Hot breaking Strength (overall absorption energy)

The composition was molded at 175° C. and 70 kg/cm$^2$ for a molding time of 2 minutes into a disk having a diameter of 70 mm and a thickness of 2 mm and post-cured at 180° C. for 4 hours. The disk was allowed to stand in a pressure cooker at 120° C. for 120 hours. Using an impact tester (manufactured by Toyo Seiki K.K. ), the overall absorption energy of the disk was determined at 170° C.

TABLE 1

| Composition (pbw) | Run No. 1 | 2 | 3 | 4 | 5* | 6* |
| --- | --- | --- | --- | --- | --- | --- |
| Epoxy resin BREN-S | 10.0 | 10.0 | 10.0 | 10.0 | 10.0 | 10.0 |
| EOCN7000 | 58.9 | 58.9 | 58.9 | 58.9 | 58.9 | 58.9 |
| Phenolic resin TD2131 | 31.1 | 31.1 | 31.1 | 31.1 | 31.1 | 31.1 |
| Silica powder | | | | | | |
| treated with D | 700 | — | — | — | — | — |
| treated with E | — | 700 | — | — | — | — |
| treated with F | — | — | 700 | 700 | — | — |
| untreated | — | — | — | — | 700 | — |
| treated with KBM-403 | — | — | — | — | — | 700 |
| Triphenylphosphine | 0.8 | 0.8 | 0.8 | 0.8 | 0.8 | 0.8 |
| Carnauba wax | 3.7 | 3.7 | 3.7 | 3.7 | 3.7 | 3.7 |
| KBM-403 | 2 | 2 | 2 | — | 2 | 2 |
| Organic silicon compound F | — | — | — | 4 | — | — |
| Properties | | | | | | |
| Water absorptivity (%) | 0.49 | 0.49 | 0.51 | 0.48 | 0.50 | 0.60 |
| Dielectric dissipation factor tan δ at 60 Hz (× 10³) | 12.00 | 4.17 | 4.76 | 4.00 | 47.58 | 800 |
| Overall absorption energy (J) | 1.20 | 1.19 | 1.23 | 1.30 | 0.972 | 0.964 |

*outside the scope of the invention

As seen from Table 1, epoxy resin compositions having improved crack resistance, thermal impact resistance and soldering resistance after moisture absorption are obtained by surface treating silica with the organic silicon compounds according to the present invention since the interaction between epoxy resin and silica at their interface is enhanced.

The organic silicon compounds according to the present invention are thus useful as resin modifiers, adhesive aids for epoxy resins or the like, and silane coupling agents. Inorganic fillers treated with the organic silicon compounds according to the present invention have enhanced interfacial interaction with resins, ensuring resin compositions having improved crack resistance, thermal impact resistance and soldering resistance after moisture absorption.

Although some preferred embodiments have been described, many modifications and variations may be made thereto in the light of the above teachings. It is therefore to be understood that within the scope of the appended claims, the invention may be practiced otherwise than as specifically described.

We claim:

1. An organic silicon compound of the following general formula (1):

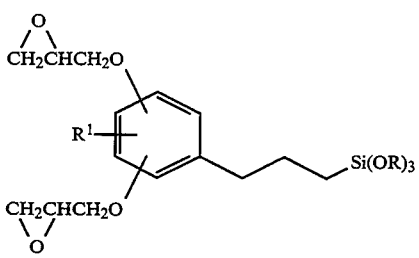

(1)

wherein $R^1$ is selected from the group consisting of a hydrogen atom, a substituted or unsubstituted monovalent hydrocarbon radical having 1 to 6 carbon atoms, and a halogen atom, and
    R is a substituted or unsubstituted monovalent hydrocarbon radical having 1 to 6 carbon atoms.

2. The organic silicon compound according to claim 1, wherein $R^1$ and R are independently selected from the group consisting of methyl, ethyl, propyl, t-butyl, propenyl and phenyl.

3. The organic silicon compound according to claim 1 that is obtained by the steps comprising:
    i) adding an allyl to a dihydroxybenzene of formula (2):

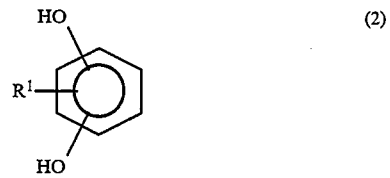

(2)

wherein $R^1$ is selected from the group consisting of a hydrogen atom, a substituted or unsubstituted monovalent hydrocarbon radical having 1 to 6 carbon atoms, and a halogen atom, to obtain a compound of formula (3):

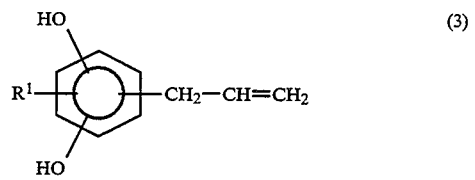

(3)

wherein $R^1$ is defined above,
    ii) epoxidizing the resultant addition product of formula (3) in the presence of a dehydrochlorination agent to obtain a compound of formula (4):

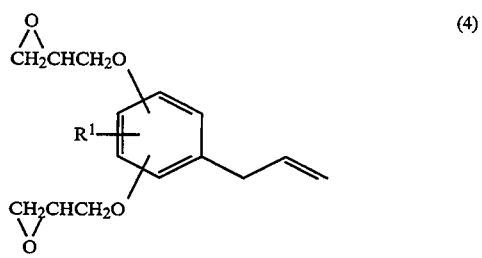

(4)

wherein $R^1$ is defined above, and
  iii) reacting said compound of formula (4) and a hydroalkoxysilane of formula (5):

HSi(OR)$_3$  (5)

wherein R is a substituted or unsubstituted monovalent hydrocarbon radical having 1 to 6 carbon atoms, to obtain said organic silicon compound of formula (1).

4. The organic silicon compound according to claim 1 having the formula

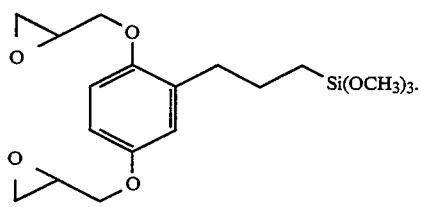

5. The organic silicon compound according to claim 1 having the formula

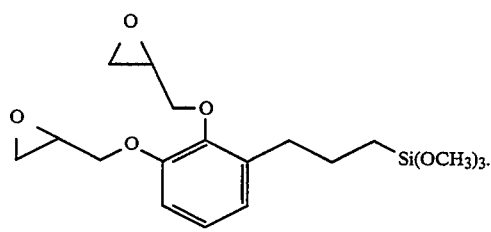

6. The organic silicon compound according to claim 1 having the formula

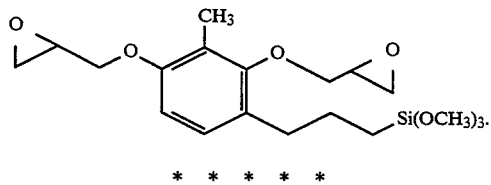

* * * * *